United States Patent

Henf

(10) Patent No.: US 10,046,286 B2
(45) Date of Patent: Aug. 14, 2018

(54) CONDITIONING MODULE FOR REGULATING THE TEMPERATURE OF AND HUMIDIFYING A FLOWING GAS

(71) Applicant: Dräger Safety AG & Co. KGaA, Lübeck (DE)

(72) Inventor: Dirk Henf, Lübeck-Travemünde (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 52 days.

(21) Appl. No.: 15/284,825

(22) Filed: Oct. 4, 2016

(65) Prior Publication Data

US 2017/0095778 A1 Apr. 6, 2017

(30) Foreign Application Priority Data

Oct. 5, 2015 (DE) ........................ 10 2015 012 783

(51) Int. Cl.
*B01F 3/04* (2006.01)
*A61M 16/00* (2006.01)
*B01F 5/06* (2006.01)
*B01F 15/06* (2006.01)
*A61M 16/16* (2006.01)
*A61M 16/10* (2006.01)

(52) U.S. Cl.
CPC ..... *B01F 3/04007* (2013.01); *A61M 16/0003* (2014.02); *A61M 16/108* (2014.02); *A61M 16/109* (2014.02); *A61M 16/16* (2013.01); *B01F 3/04049* (2013.01); *B01F 5/06* (2013.01); *B01F 15/065* (2013.01); *A61M 2205/3368* (2013.01); *A61M 2205/3606* (2013.01); *A61M 2205/366* (2013.01); *A61M 2205/70* (2013.01); *A61M 2209/02* (2013.01); *B01F 2015/061* (2013.01); *B01F 2015/062* (2013.01)

(58) Field of Classification Search
CPC .... B01F 3/04; B01F 3/04007; B01F 3/04021; B01F 3/04049
USPC ............................................ 261/112.1, 114.1
See application file for complete search history.

(56) References Cited

U.S. PATENT DOCUMENTS 5,535,989 A * 7/1996 Sen ........................ B01D 3/008
261/112.1

FOREIGN PATENT DOCUMENTS

| CN | 204 460 413 U | 7/2015 |
|----|---------------|--------|
| DE | 24 49 041 A1 | 4/1976 |
| DE | 36 34 377 C2 | 3/1988 |
| EP | 2 065 082 A1 | 6/2009 |
| EP | 1 506 805 B1 | 12/2011 |
| JP | S63-151 328 A | 6/1988 |

* cited by examiner

*Primary Examiner* — Robert A Hopkins
(74) *Attorney, Agent, or Firm* — McGlew and Tuttle, P.C.

(57) ABSTRACT

A conditioning module (1), for regulating the temperature of and humidifying a flowing gas (60), has a flowthrough body (10) with an inflow opening (11) and with an outflow opening (12). The inflow opening (11) is connected to a gas feed line (2) in a fluid-communicating manner and the outflow opening (12) is connected to a gas outflow line (3) in a fluid-communicating manner. A lower inner area (13) of the flowthrough body (10) is configured as a collecting tank (14) for collecting water (62).

19 Claims, 2 Drawing Sheets

CONDITIONING MODULE FOR REGULATING THE TEMPERATURE OF AND HUMIDIFYING A FLOWING GAS

CROSS REFERENCE TO RELATED APPLICATIONS

This application claims the benefit of priority under 35 U.S.C. § 119 of German Application 10 2015 012 783.7 filed Oct. 5, 2015, the entire contents of which are incorporated herein by reference.

FIELD OF THE INVENTION

The present invention pertains to a conditioning module for regulating the temperature of and humidifying a flowing gas, having a flowthrough body with an inflow opening and with an outflow opening, wherein the flow opening is connected to a gas feed line in a fluid-communicating manner and the outflow opening is connected to a gas outflow opening in a fluid-communicating manner, and wherein a lower inner area of the flowthrough body is configured as a collecting tank for collecting water.

BACKGROUND OF THE INVENTION

Devices for simulating pulmonary activities and/or pulmonary functions are known, in principle, in modern technology. Such lung simulators, which can provide especially a sinusoidal motion of air, i.e., a motion similar to that seen in a human being, in the form of inhalation and exhalation, are used, for example, in breathing simulators, which are used especially for a function test and/or approval test of respirators, for example, closed-circuit devices. In respirators, which are configured as such a closed-circuit device, especially as a closed-circuit device that is independent from the ambient air, the consumed air is not released into the surrounding area, as, for example, in respirators operating with compressed air, but is reprocessed in the respirator. For example, especially oxygen is added and carbon dioxide is adsorbed during such a processing. To make it possible to carry out a function and/or approval test in case of a closed-circuit device, an exhaled air must therefore be simulated. In particular, the temperature of the air must be regulated to about 37° C. and the relative humidity of the air must be set at about 90% to 100%. Conditioning modules are frequently used to achieve this.

Regulating the temperature of and humidifying a gas, especially air, is known, in principle. For example, gases can thus be passed through a plurality of thin tubes made of a membrane material, which are surrounded by water, whose temperature is regulated, for humidifying gases for fuel cells. Humidity is transported through the membrane into the gas in the tubes. It is, however, disadvantageous here that a high flow resistance develops for the gas due to the use of the thin tubes. Further, it is known that water with a regulated temperature can be injected into an air stream. Such devices are used, for example, in medical devices for ventilating patients. It is, however, disadvantageous here that the temperature regulation and humidification of only a small volume flow of gas can be achieved. Larger volume flows can be handled only by the use of a plurality of these devices. Another possibility, often used in conditioning modules, is to pass the water over a tank containing water with a regulated temperature. Heating and humidification of the gas takes place due to flowing over the surface of the water and the rise in humidity due to the take-up of water vapor from the liquid by the flowing gas taking place in the process. An increase in the amount of conditioned volume flow can only be achieved by enlarging the entire device in this case as well.

In an approval test for respirators, there are specifications, especially legal ones, concerning, for example, a maximum gas volume of the test set-up used and/or a maximum flow resistance of the device. Providing larger volume flows, which are likewise often necessary according to the specifications, solely by a corresponding scale-up of the device used thus has limitations, at least in this field of use.

SUMMARY OF THE INVENTION

Based on this state of the art, a basic object of the present invention is to eliminate these drawbacks at least partially in conditioning modules. Therefore, an object of the present invention is to provide a conditioning module, which generates a large volume flow of temperature-regulated and humidified gas in an especially simple and favorable manner and which especially has at the same time the smallest possible total gas volume as well as the lowest possible flow resistance.

According to the present invention, the object is accomplished by a conditioning module for regulating the temperature of and humidifying a flowing gas, having a flowthrough body with an inflow opening and with an outflow opening, wherein the inflow opening is connected to a gas feed line in a fluid-communicating manner and the outflow opening is connected to a gas outflow line in a fluid-communicating manner, and wherein a lower inner area of the flowthrough body is configured as a collecting tank for collecting water. A conditioning module according to the present invention is characterized in that the conditioning module has a delivery device for delivering water, wherein, in addition to the collecting tank, at least one additional inner wall area of the flowthrough body is wettable with water by the delivery device in at least some sections.

A conditioning module according to the present invention may be used, for example, in a breathing simulator. A gas flows through a flowthrough body of the conditioning module and its temperature of the gas is regulated and the gas is humidified in this. The flowthrough body is configured for this at least partially as a hollow body. A gas feed line is connected to an inflow opening of the flowthrough body in a fluid-communicating manner, so that the gas can flow into the interior of the flowthrough body. The gas temperature is regulated and the gas is humidified in the flowthrough body and can again flow out of the interior of the flowthrough body through an outflow opening, which is connected to a gas discharge line in a fluid-communicating manner. The inflow opening and the outflow opening may preferably be arranged opposite each other on the flowthrough body. Guiding devices for distributing and guiding the gas in the interior of the flowthrough body may also be provided, especially in order to provide an especially good and uniform distribution and/or flow of the gas in the interior of the flowthrough body. A lower inner area of the flowthrough body is configured as a collecting tank for collecting water. The collecting tank may comprise here, for example, only at least one drain, through which water can flow off from the interior of the flowthrough body. The collecting tank may, of course, also be configured for taking up water, as a result of which a water surface can be formed in the interior of the flowthrough body. Temperature regulation and release of humidity to the gas flowing past can be further improved hereby.

Provisions are made according to the present invention for the conditioning module to have a delivery device for delivering water. Delivery of water according to the present invention comprises here especially the distribution of water and/or motion of the water especially to a distribution point in the flowthrough body. The delivery device has all the necessary components, for example, pipes, valves, pumps or the like, which are necessary for such a delivery. The delivery device may preferably be arranged, at least in some of its sections, in the interior of the flowthrough body. It can be made possible hereby, in particular, to distribute water in the interior of the flowthrough body. Provisions are made, in a manner essential for the present invention, for at least one additional inner wall area of the flowthrough body to be wettable with water, in at least some sections, by the delivery device. In other words, the delivery device is configured for wetting the at least one additional wall area with water. For example, water can thus be applied, for example, sprayed onto this additional inner wall area by the delivery device. The water can thus be distributed on the surface of the wall area and thereby exposed to the gas flowing in the flowthrough body. Provisions may, of course, be made for the water, obeying, for example, the force of gravity, to move downward over the at least one additional wall area until it reaches the lower area of the flowthrough body and is collected in the collecting tank. The additional inner wall area of the flowthrough body, for example, an area of a side wall of a cavity in the interior of the flowthrough body, is a section different from the collecting tank according to the present invention in the interior of the flowthrough body. Since water can be applied to this additional inner wall area by the delivery device, a total area, which is wettable with water, will thus be obtained in the interior of the flowthrough body at least from the sum of the areas of the collecting tank and of the at least one additional inner wall area. The total area, which is available for the wetting with water, can thus be increased. It can be made possible in an especially simple manner due to such a larger area wettable with water for a gas flowing past to take up more moisture. Saturation of the gas, i.e., a relative humidity of at least approximately 100%, can thus be reached more rapidly, especially without having to increase the volume of the flowthrough body. At the same time, a temperature regulation of the flowing gas can also be achieved by a corresponding temperature regulation, for example, heating, of the water, which is especially delivered by the delivery device. This can also be made possible by a conditioning module according to the present invention in an especially compact manner.

Provisions may especially preferably be made in a conditioning module according to the present invention for the conditioning module to be configured for regulating the temperature of and humidifying air as a flowing gas. Air is defined according to the present invention especially as a gas composition that corresponds, especially concerning the relative quantities of nitrogen, oxygen and/or carbon dioxide, at least essentially to the composition of an ambient air. It can be made possible in this manner to simulate a breathing air, especially exhaled air, of a person. The use of a conditioning module according to the present invention in a breathing simulator, for example, for a function test and/or approval test of a respirator, can be made possible hereby in an especially simple manner.

A conditioning module according to the present invention may also be configured such that the delivery device is configured for forming, in at least some sections, a water film on the at least one additional inner wall area. A water film according to the present invention is essentially a closed water surface of a small thickness, which is arranged on a surface of the at least one additional inner wall area. The area of the water over which the gas flows can be increased even further in this manner. Very good humidification and temperature regulation of the gas van be achieved hereby.

According to an especially preferred variant of a conditioning module according to the present invention, provisions may, furthermore, be made for the at least one additional inner wall area of the flowthrough body to be arranged sloped, especially by 90°, in at least some sections, in relation to the lower, inner area of the flowthrough body. The lower area of the flowthrough body is configured as a collecting tank for water. To make it possible to collect and especially absorb the water in the collecting tank, the lower area is therefore preferably configured at least more or less horizontally in at least some sections. Water, especially a water film, which is applied to an inner wall area, which is sloped in this lower area, especially by 90°, will therefore flow off to the collecting tank. The absorption of moisture in the flowing gas is facilitated by this flowing in, especially by the kinetic energy present in the water as a result. Further, this arrangement has especially the advantage that new water can continuously be applied by the delivery device to the wall area without an unwanted retention of water occurring on the wall area. Due to the possibility of a continuous replacement of the water, especially in the water film, it is possible, for example, to set and/or change the temperature of the water being used in the flowthrough body especially rapidly. An especially good and especially rapid control and/or regulation of the humidification and temperature regulation of a flowing gas by a conditioning module according to the present invention can thus be made available.

Further, a conditioning module according to the present invention may preferably be configured such that the delivery device has at least one rising pipe, an outer surface of the rising pipe forming, in at least some sections, a part of the at least one inner wall area. A rising pipe may be preferably a hollow, especially at least essentially cylindrically symmetric component, which is configured in its interior for transporting water. A rising pipe according to the present invention is preferably arranged in the interior of the flowthrough body and at an angle of about 90° in relation to the lower area or to the collecting tank. Due to the fact that an outer surface of the rising pipe forms, according to the present invention, a part of the at least one inner wall area in at least some sections, the inner wall area can be expanded additionally and in an especially simple manner, especially without the volume enclosed in the flowthrough body having to be enlarged. Since, furthermore, the delivery device is configured for wetting this inner wall area, humidification of the flowing gas by a conditioning module according to the present invention can be further improved and the conditioning module according to the present invention can at the same time be configured in a compact form.

According to one variant, provisions may, furthermore, be made in a conditioning module according to the present invention for the at least one rising pipe to have a water distribution device, especially a mushroom fountain head, at an upper end. It can be achieved through such a water distribution device that the water being transported in the rising pipe will be better distributed. Mushroom fountain heads, i.e., devices for radially distributing liquids, are especially suitable water distribution devices, especially due to their small overall height. In particular, it can be achieved thereby in an especially simple manner, for example, in case of a cylindrical rising pipe, that a water film formed fully circumferentially will become established on the outer wall of the rising pipe. It can additionally be achieved due to the use of a mushroom fountain head that the height of the inner cavity of the flowthrough body can also be utilized in the best possible manner and as completely as possible for arranging the rising pipe. An especially large configuration and an especially good utilization of the entire outer surface of the at least one rising pipe as an additional inner wall area can be made possible thereby.

A conditioning module according to the present invention may also be perfected such that the at least one rising pipe is formed of a plastic material, a glass material, a metal, a metal alloy, preferably special steel. Glass materials as well as special steel as the material for the at least one rising pipe has the advantage of good resistance to corrosion. In particular, a glass material is advantageous for the at least one rising pipe, because glass materials have great tightness against gases and liquids along with high stability. As a result, such a rising pipe made of a glass material can be configured with an especially thin wall and thus it requires only a small space for installation. A water distribution device, especially a mushroom fountain head, may preferably be manufactured from a porous glass material. A rising pipe made of a glass material, especially one configured with a water distribution device, can thus be configured especially easily and in a space-saving manner, as a result of which especially the volume in the interior of the flowthrough body, which is available for the flowing gas, is limited only slightly and especially not needlessly. A flow resistance, which is generated by the flowthrough body, can, furthermore, be prevented in this manner from being needlessly increased.

Further, provisions may be made according to a preferred variant of a conditioning module according to the present invention for the delivery device to have two or more, especially 24 to 32 and preferably 28 rising pipes. Due to the provision of two or more rising pipes, the additional inner wall area can be enlarged by the outer walls of the plurality of rising pipes. An even better humidification and temperature regulation of the flowing gas can thus be efficiently achieved. If limitations of a maximum possible gas volume are taken into account, for example, with respect to a approval test for respirators, it was found that the best results can be obtained concerning humidification and temperature regulation of the flowing gas with 24 to 32 rising pipes and preferably with 28 rising pipes.

Moreover, a conditioning module according to the present invention may be configured such that an inner side wall of the flowthrough body forms, in at least some sections, a part of the at least one additional inner wall area and that the delivery device has a distribution element, which is configured for wetting the side wall with water, said distribution element being arranged especially in and/or on an upper section of the side wall. Such a distribution element may, of course, also be arranged on a plurality of inner side walls, especially on all inner side walls of the flowthrough body. It can be made possible in this manner to also use the inner side walls of the flowthrough body, especially of a cavity in the flowthrough body, as additional wall areas and thus to use these to humidify the flowing gas and to regulate its temperature. The area wetted by water, especially the area covered by a water film, can be enlarged hereby in an especially simple manner. Especially due to an arrangement in and/or on an upper section of the side wall, it is also possible to use at least a major part of the height of the side wall as an additional inner wall area. The distribution element may advantageously also extend along the entire side wall or at least essentially along the entire side wall. As a result, wetting preferably of the entire side wall with water, especially generation of a water film on the lateral surface, by a distribution element can be provided hereby in an especially simple manner. Such a distribution element may be, for example, a pipe, which is provided, for example, with holes, through which water can escape. The holes may preferably be arranged in the direction or at least essentially in the direction of the side wall. A water film can be generated hereby on the surface of the side wall in an especially simple manner.

Further, provisions may be made in a conditioning module according to the present invention for the delivery device to be able to be supplied with water from a water reservoir, the water reservoir being especially arranged outside the flowthrough body. The delivery device can be supplied with water in this way in an especially simple manner. The water reservoir may be configured here, for example, as a closed tank, which is connected to the delivery device in a fluid-communicating manner. Due to the water reservoir being arranged outside the flowthrough body, it can be achieved, in particular, that the volume available for the flow of gas in the flowthrough body will not be reduced. The flow of gas in the flowthrough body can thus be prevented from being influenced both in terms of a total volume and of the flow resistance.

A conditioning module according to the present invention may also be perfected such that a pump device is arranged between the collecting tank and the water reservoir. Provisions are, of course, made in this case for the pump device to be connected to the collecting tank and to the water reservoir in a fluid-communicating manner. Water can preferably be pumped off from the collecting tank by the pump device and discharged into the water reservoir. A pressure can also be applied hereby to the water in the water reservoir. This has the advantage, for example, in case of a delivery device with at least one rising pipe, that the water is pressed hereby from the water reservoir into the at least one rising pipe and it will be discharged again, preferably by a water distribution device, at the other end of the rising pipe in the interior of the flowthrough body. Distribution elements on the inner side walls of the flowthrough body can thus also be supplied with water in an especially simple manner. Since water, which wets a wall area in the interior of the flowthrough body due to the delivery device, is preferably collected subsequently in the collecting tank, a closed water circuit can thus be provided. The quantity of water needed for humidifying the flowing gas can be reduced thereby.

Further, provisions may be made in a preferred variant of a conditioning module according to the present invention for the conditioning module to have an especially regulatable temperature regulation device for regulating the temperature of water in the water reservoir and/or in the collecting tank. The temperature of the water being used can be set in this way in an especially simple manner. The temperature of the water is regulated in the water reservoir and/or in the collecting tank, for example, to about 40° C., and is then distributed via the delivery device on the at least one additional inner wall surface. The temperature of the water being used, which temperature is especially uniform in the entire flowthrough body, can be achieved hereby in an especially simple manner.

A conditioning module according to the present invention may also be configured such that at least one temperature regulation line is arranged outside the flowthrough body, wherein the temperature regulation line is connected to the gas feed line and to the gas outflow line in a fluid-communicating manner, especially connected in a regulatably fluid-communicating manner. It can be made possible by such a temperature regulation line, in particular, that gas can be sent from the gas feed line into the gas outflow line without humidification in the flowthrough body. It is possible in this manner to regulate the humidity of the gas in the gas outflow line, and especially to reduce an excessively high humidity of the gas in the gas outflow line by introducing non-humidified gas from the temperature regulation line. It can be made possible hereby to provide flowing gas even more correctly according to the demand, especially in terms of the humidity of the gas.

A conditioning module according to the present invention can be especially preferably perfected such that the at least one temperature regulation line is configured as a cooling pipe with a cooling device and/or the at least one temperature regulation line is configured as a heating pipe with a heating device. Especially the cooling of a gas in the temperature regulation line configured as a cooling pipe can be made possible by such a cooling device. In particular, heating of a gas in the temperature regulation line configured as a heating pipe can correspondingly be made possible by such a heating device. Due to the at least one temperature regulation line being configured as a cooling pipe and/or as a heating pipe, it can thus be made possible to also change the temperature of the gas passed by the flowthrough body in the temperature regulation line. At least one temperature regulation line is especially preferably arranged as a cooling pipe and at least one temperature regulation line as a heating pipe between the gas feed line and the gas outflow line in a conditioning module according to the present invention and each is connected to these lines in a fluid-communicating manner. The temperature of the gas in the gas outflow line can both be increased and reduced by introducing gas from the corresponding temperature regulation line. The supply of flowing gas, especially in terms of the temperature of the gas, according to the demand can thus be improved even more.

Further, provisions may especially preferably be made in a variant of a conditioning module according to the present invention for the heating pipe to be arranged, in at least some sections, in the water reservoir. A temperature regulation device may preferably also be arranged now in the water reservoir. In particular, the water reservoir can assume hereby the function of a heating device for the heating pipe. An additional heating device at the heating pipe can be eliminated.

Further measures improving the present invention appear from the following description of exemplary embodiments of the present invention, which are shown in the figures. All the features and/or advantages appearing from the claims, the description or the drawings, including design details and arrangements in space, may be essential for the present invention both in themselves and in different combinations.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
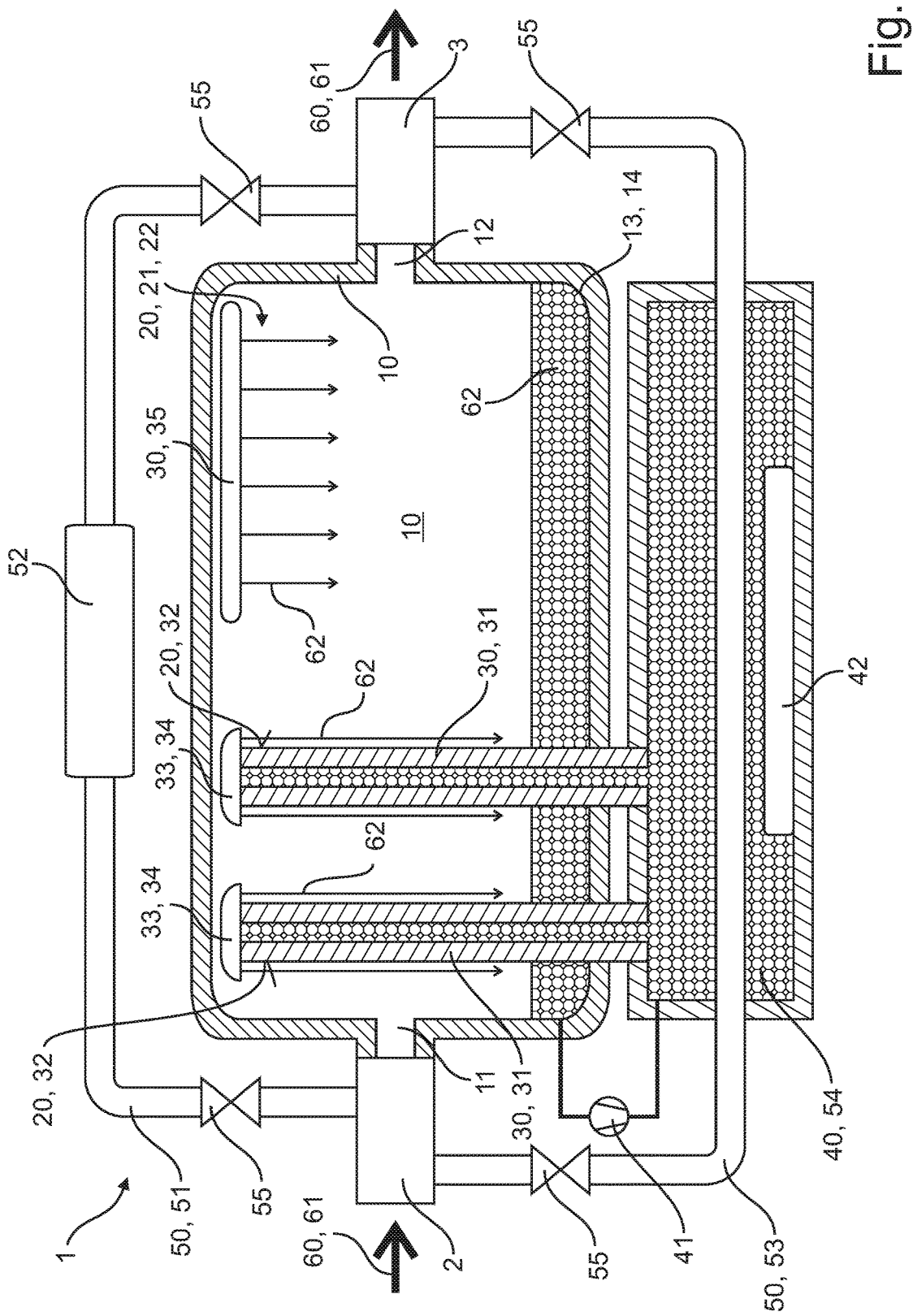
FIG. 1 is a sectional view of a conditioning module according to the present invention.

Referring to the drawings, FIG. 1 shows a conditioning module 1 according to the present invention with a flowthrough body 10. A gas 60, especially air 61, can be humidified and its temperature can be regulated in the conditioning module 1. For this, the flowthrough body 10 has an inflow opening 11, which is connected to a gas feed line 2 in a fluid-communicating manner. The gas 60 flows through the inflow opening 11 into the flowthrough body 10 and is humidified and a temperature of the gas is regulated in the interior of the flowthrough body 10 and then the gas flows out of the flowthrough body 10 through an outflow opening 12, which is connected to a gas outflow line 3 in a fluid-communicating manner. A plurality of delivery devices 30, which are configured for wetting an inner wall area 20 of the flowthrough body 10, are arranged in the interior of the flowthrough body 10, which is configured as a hollow body. The individual delivery devices 30 are shown schematically and as examples, and, in particular, additional such delivery devices 30 may also be provided in embodiments of a conditioning module 1 according to the present invention. Two of the delivery devices 30 are configured as rising pipes 31. The rising pipes 31 especially have a cylindrical configuration and have each at an upper end a water distribution device 33, which is configured as a mushroom fountain head 34. The rising pipes 31 are preferably manufactured from a glass material, as a result of which they can be made, in particular, especially thin-walled. A quantity of water 62 is transported upward in the interior of the rising pipes 31, radially distributed in the mushroom fountain heads 34, and the water subsequently flows downwards, especially as a water film 62, on an outer surface 32 of the rising pipe 31. The outer surfaces 32 of the rising pipes 31 thus form an inner wall area 20, which is wetted with water by a delivery device 30. The water 62 is caught and collected in a lower area 13 of the flowthrough body 10, which is configured as a collecting tank 14. Humidification and temperature regulation of the gas 60 is likewise possible when it flows over the surface of the water 62 in the collecting tank 14. However, the gas 60 can be additionally humidified and the gas temperature can also be regulated due to the presence according to the present invention of a delivery device 30, which is configured for wetting at least one additional inner wall area 20 with water 62. The humidification and the temperature regulation of the gas 60 can thus be improved without the volume of the conditioning module 1, especially of the flowthrough body 10, having to be enlarged. A delivery device 30 of a conditioning module 1 according to the present invention can be supplied with water 62 from, for example, a water reservoir 40. This is shown directly for the rising pipes 31 shown. The water pressure necessary for the delivery of water 62 in the rising pipes 31 can be provided by a pump device 41. As is shown in the embodiment shown, this pump device is arranged between the collecting tank 14 and the water reservoir 40 in a fluid-communicating manner. Water 62, which is introduced via the delivery devices 30 into the interior of the flowthrough body 10, collects in the collecting tank 14 and is delivered by the pump device 41 into the water reservoir 40. An overpressure, which makes possible the transportation of the water 62 to the mushroom fountain head 34 arranged at the tip of the respective rising pipe 31, becomes established there. On the whole, even a closed-circuit operation can be provided in this manner with respect to the water 62 used.

A distribution element 35 is shown as another possible embodiment of a delivery device 30. The distribution element 35 may, of course, also be connected to the water reservoir 40 in a fluid-communicating manner (not shown). The distribution element 35 is preferably configured with this embodiment as a pipe and is arranged in an upper section 22 of an inner side wall 21 of the flowthrough body 10. The distribution element 35 may have, for example, a plurality of holes, which preferably face the side wall 21 and thus make possible the wetting of the side wall 21 with water 62, especially with a water film 62. The inner side walls 21, especially all inner side walls 21, of the flowthrough body 10 can be used in this manner as an additional inner wall area 20. An even better humidification of the flowing gas 60 can be made possible by this additional enlargement of the area that is wettable with water 62.

The conditioning module 1 further comprises a temperature regulation means to make it possible regulate the temperature of the flowing gas 60 during the humidification of the flowing gas 60. The temperature regulation means comprises a temperature regulation device 42 is arranged in the water reservoir 40. The temperature of the water 62 used in the delivery devices 30 can be set thereby, as a result of which the temperature of the flowing gas 60 can automatically be changed as well. Since, as was described above, the water 62 is especially circulated in a closed-circuit operation, the inner wall areas 20 are always wetted with fresh water 62 from the water reservoir 40. Temperature changes, for example, those caused by a change in the setting of the temperature regulation device 42, can thus be transmitted especially rapidly to the gas 60 flowing through the flowthrough body 10. Moreover, the embodiment of a conditioning module according to the present invention 1 shown has two temperature regulation lines 50, which are each connected to both the gas feed line 2 and the gas outflow line 3 in a fluid-communicating manner. These are part of a temperature regulation means to make it possible regulate the temperature of the flowing gas during the humidification of the flowing gas, which may be used instead of or with the above described temperature regulation means. With the two temperature regulation lines, a flow of gas 60 from the gas feed line 2 to the gas outflow line 3 can also be made possible without a flow through the flowthrough body 10. This results, in particular, in the gas 60 not being humidified in the temperature regulation lines 50. The entry and discharge of gas 60 into and out of one of the respective temperature regulation lines 50 is controlled, especially regulated, by valves 55. The valves 55 are actuated and regulated with this embodiment such that the gas 60 is forcibly guided through the flowthrough body 10 and the temperature regulation lines 50. As a result, regulation of the relative humidity of the gas 60 in the gas outflow line 3 can be made possible. In particular, an especially high moisture content in the gas 60, which comes from the flowthrough body 10, can be compensated by introducing non-humidified gas 60 from one of the temperature regulation lines 50. One of the temperature regulation lines 50 is configured in this case as a cooling pipe 51 and the second temperature regulation line 50 is configured as a heating pipe 53. The cooling pipe 51 has, in particular, a cooling device 52, which is configured to cool the gas 60 in the cooling pipe 51. Analogously to this, the heating pipe 53 has a heating device 54 for heating the gas 60 in the heating pipe 53. This heating device 54 is provided in this embodiment by the heating pipe 53 being led in some sections through the temperature-regulated water reservoir 40, which is especially heated to preferably about 40° C. by the temperature regulation device 42. The temperature of the flowing gas 60 can also be set and especially regulated in the gas outflow line 3 by a corresponding introduction from the cooling pipe 51 or from the heating pipe 53. Sensors for monitoring both the humidity and the temperature of the gas 60 (not shown) may, of course, be arranged in both the gas feed line 2 and the gas outflow line 3. On the whole, especially good humidification and temperature regulation of a flow gas 60, especially air 61, can be provided by a conditioning module 1 according to the present invention, and an especially compact configuration of a conditioning module 1 according to the present invention is made possible especially by the use of the additional inner wall area 20 during the humidification and temperature regulation of the gas 60. Further, the relative humidity and the temperature of the flowing gas 60 can also be set, especially set in a regulated manner, especially well and in an especially simple manner due to the presence of temperature regulation lines 50.

Figure 2:
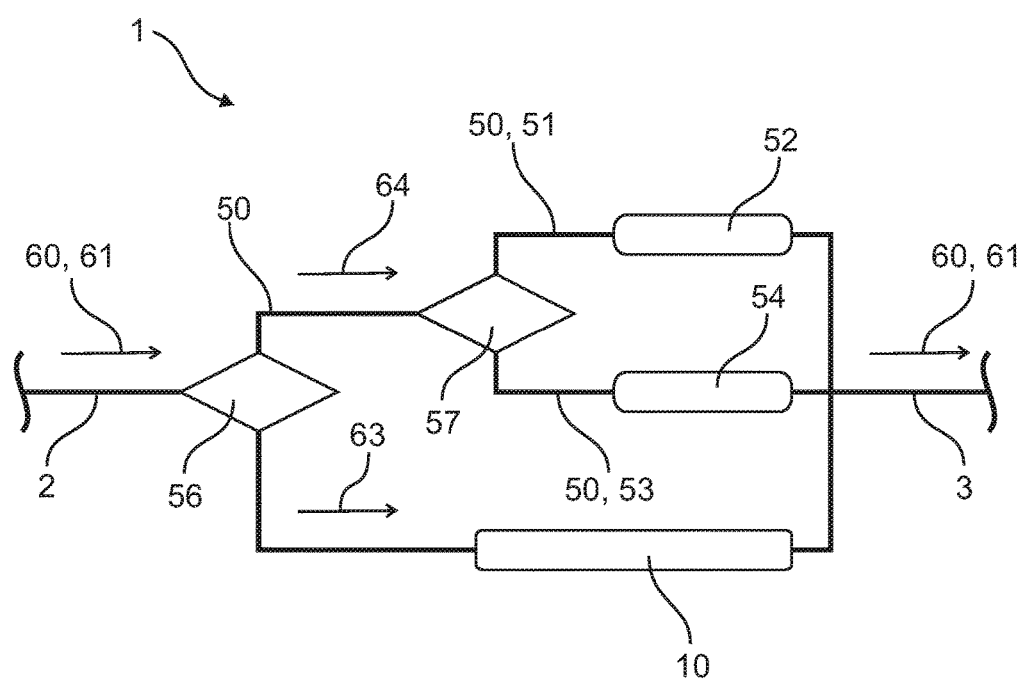
FIG. 2 is a block diagram of a conditioning module according to the present invention.

FIG. 2 shows a block diagram of another possible embodiment of a conditioning module 1 according to the present invention. The conditioning module 1 used may be configured here, with the exception of the guiding of the gas 60, like the conditioning module 1 shown in FIG. 1 and is shown only schematically. Reference is therefore made to FIG. 1 with respect to the description of the conditioning module 1 and the components thereof.

According to the block diagram shown, proportional valves 56, 57 are used to ensure the forced guiding of the flow of gas 60, which may, in turn, preferably be air 61. A first proportional valve 56 is used with this embodiment to regulate the humidity in order to split a stream of gas 60 arriving from the gas feed line 2 into a first part 63, which is to be humidified and which is fed to the flowthrough body 10, and a second part 64, which is not to be humidified and is sent to the temperature regulation lines 50. The second part 64 is split again subsequent hereto in a proportional valve 57 for temperature regulation between temperature regulation lines 50, which are configured as a cooling pipe 51 with a cooling device 52 and as a heating pipe 53 with a heating device 54. As an alternative, provisions may also be made here for the cooling pipe 51 to be configured without a cooling device 52. Following the flowthrough body 10, the cooling pipe 51 and the heating pipe 53, the individual streams of the gas 60 are converged again in a gas outflow line 3. Since proportional valves 56, 57 are used to split the gas 60 among the individual flow paths, forced guiding of the gas 60 is obtained through the entire conditioning module 1. Sensors may, of course, be arranged (not shown) in both the gas feed line 2 and in the gas outflow line 3 for monitoring both the humidity and the temperature of the gas 60. Due to a corresponding splitting of the gas 60 between the first part 63, which is to be humidified, and the second part 64, which is not to be humidified, by the proportional valve 56, the humidity of the gas 60 in the gas outflow line 3 can be set, especially set in a regulated manner, in an especially simple manner. Moreover, the temperature of the flowing gas 60 in the gas outflow line 3 can also be set, especially set in a regulated manner, especially well and in an especially simple manner due to a corresponding additional splitting of the second part 64 of the gas 60 between the cooling pipe 51 and the heating pipe 53.

While specific embodiments of the invention have been shown and described in detail to illustrate the application of the principles of the invention, it will be understood that the invention may be embodied otherwise without departing from such principles.

APPENDIX

List of Reference Numbers

1 Conditioning module
2 Gas feed line
3 Gas outflow line
10 Flowthrough body
11 Inflow opening
12 Outflow opening
13 Area
14 Collecting tank
20 Wall area
21 Side wall
22 Section
30 Delivery device
31 Rising pipe
32 Outer surface
33 Water distribution device
34 Mushroom fountain head
35 Distribution element
40 Water reservoir
41 Pump device
42 Temperature regulation device
50 Temperature regulation line
51 Cooling pipe
52 Cooling device
53 Heating pipe
54 Heating device
55 Valve
56 Proportional valve (humidity regulation)
57 Proportional valve (temperature regulation)
60 Gas
61 Air
62 Water
63 First part
64 Second part

What is claimed is:

1. A conditioning module for regulating a temperature of a flowing gas and humidifying the flowing gas, the conditioning module comprising:
   a flowthrough body with an inflow opening and with an outflow opening, wherein the inflow opening is conducted to a gas feed line in a fluid-communicating manner and the outflow opening is connected to a gas outflow line in a fluid-communicating manner, and wherein the flowthrough body includes a lower inner area configured as a collecting tank collecting water; and
   a delivery device delivering water to the collecting tank and wetting the lower inner area in at least some sections and delivering water to at least one additional inner surface and wetting at least a section of the at least one additional inner surface, wherein the delivery device comprises at least one rising pipe, wherein an outer surface of the rising pipe forms, in at least some sections, a part of the at least one inner surface.

2. A conditioning module in accordance with claim 1, further comprising a temperature regulation means for regulating a temperature of the flowing gas during humidification of the flowing gas whereby the conditioning module is configured for regulating the temperature of the flowing gas and humidifying the flowing gas.

3. A conditioning module in accordance with claim 1, wherein the at least one inner surface is at least one inner wall and the delivery device is configured for forming a water film at the at least a section of the at least one additional inner wall.

4. A conditioning module in accordance with claim 1, wherein the at least one inner surface is at least one additional inner wall of the flowthrough body that is arranged, in at least some sections, sloped in relation to the lower inner area of the flowthrough body.

5. A conditioning module in accordance with claim 1, wherein the at least one inner surface is at least one additional inner wall of the flowthrough body angled, in at least some sections, at an angle or about 90° in relation to the lower inner area of the flowthrough body.

6. A conditioning module in accordance with claim 1, wherein the at least one rising pipe has a water distribution device comprising a mushroom fountain head at an upper end the at least one rising pipe.

7. A conditioning module in accordance with claim 1, wherein the at least one rising pipe consists essentially of a plastic material, a glass material, a metal, a metal alloy.

8. A conditioning module in accordance with claim 1, wherein the at least one rising pipe consists essentially special steel.

9. A conditioning module in accordance with claim 1, wherein the delivery device comprises at least one additional rising pipe to provide a plurality of rising pipes.

10. A conditioning module in accordance with claim 1, wherein the plurality of rising pipes comprises 24 to 32 rising pipes.

11. A conditioning module in accordance with claim 1, wherein:
   the at least one inner surface is at least one additional inner wall of the flowthrough body;
   the at least one additional inner wall area comprises at least some sections of an inner side wall of the flowthrough body;
   the delivery device comprises a distribution element configured to wet the at least some sections of the inner side wall with water; and
   said distribution element is arranged in or on an upper section of the inner side wall.

12. A conditioning module for regulating a temperature of a flowing gas and humidifying the flowing gas, the conditioning module comprising:
   a flowthrough body with an inflow opening and with an outflow opening, wherein the inflow opening is conducted to a gas feed line in a fluid-communicating manner and the outflow opening is connected to a gas outflow line in a fluid-communicating manner, and wherein the flowthrough body includes a lower inner area configured as a collecting tank collecting water;
   a delivery device delivering water to the collecting tank and wetting the lower inner area in at least some sections and delivering water to at least one additional inner surface and wetting at least a section of the at least one additional inner surface; and
   a water reservoir arranged outside the flowthrough body wherein the delivery device is supplied with water from the water reservoir.

13. A conditioning module in accordance with claim 12, further comprising a pump device arranged between the collecting tank and the water reservoir.

14. A conditioning module in accordance with claim 12, further comprising a regulatable temperature regulation device regulating the temperature of water in the water reservoir or in the collecting tank or both in the water reservoir and in the collecting tank.

15. A conditioning module in accordance with claim 12, further comprising:
   at least one temperature regulation line arranged outside the flowthrough body, the temperature regulation line being regulatably and fluid-communicatingly connected to the gas feed line and to the gas outflow line, wherein
   the at least one temperature regulation line is configured as a heating pipe with a heating device; or
   the at least one temperature regulation line comprises both a cooling pipe with a cooling device and a heating pipe with a heating device; and
   the heating pipe is arranged, in at least some sections, in the water reservoir.

16. A conditioning module for regulating a temperature of a flowing gas and humidifying the flowing gas, the conditioning module comprising:
   a flowthrough body with an inflow opening and with an outflow opening, wherein the inflow opening is conducted to a gas feed line in a fluid-communicating manner and the outflow opening is connected to a gas outflow line in a fluid-communicating manner, and wherein the flowthrough body includes a lower inner area configured as a collecting tank collecting water;
   a delivery device delivering water to the collecting tank and wetting the lower inner area in at least some sections and delivering water to at least one additional inner surface and wetting at least a section of the at least one additional inner surface; and
   at least one temperature regulation line arranged outside the flowthrough body, wherein the temperature regulation line is regulatably and fluid-communicatingly connected to the gas feed line and to the gas outflow line.

17. A conditioning module in accordance with claim 16, wherein:
   the at least one temperature regulation line is configured as a cooling pipe with a cooling device; or
   the at least one temperature regulation line is configured as a heating pipe with a heating device; or
   the at least one temperature regulation line comprises both a cooling pipe with a cooling device and a heating pipe with a heating device.

18. A flowing gas temperature and humidity conditioning module comprising:
   a flowthrough body with an inflow opening and with an outflow opening, wherein the inflow opening is conducted to a gas feed line in a fluid-communicating manner and the outflow opening is connected to a gas outflow line in a fluid-communicating manner, and wherein the flowthrough body includes a lower inner area configured as a collecting tank collecting water;
   a delivery device delivering water to the collecting tank and wetting the lower inner area in at least some sections and delivering water to at least one additional inner surface and wetting at least a section of the at least one additional surface for humidification of the flowing gas; and
   a temperature regulation means for regulating a temperature of the flowing gas with the humidification of the flowing gas.

19. A conditioning module in accordance with claim 18, wherein the temperature regulation means comprises:
   a water reservoir and a regulatable temperature regulation device regulating the temperature of water in the water reservoir or in the collecting tank or both in the water reservoir and in the collecting tank; or
   one or more temperature regulation lines configured as a cooling pipe with a cooling device or configured as a heating pipe with a heating device or configured as both a cooling pipe with a cooling device and a heating pipe with a heating device; or
   any combination of a water reservoir and a regulatable temperature regulation device regulating the temperature of water in the water reservoir or in the collecting tank or both in the water reservoir and in the collecting tank and one or more temperature regulation lines configured as a cooling pipe with a cooling device or configured as a heating pipe with a heating device or configured as both a cooling pipe with a cooling device and a heating pipe with a heating device.

* * * * *